(12) United States Patent
Koch et al.

(10) Patent No.: US 9,474,889 B2
(45) Date of Patent: Oct. 25, 2016

(54) SEALING ARRANGEMENT FOR MEDICAL INTRODUCER

(75) Inventors: Durmus Koch, Demarest, NJ (US); Cagdas Gayretli, Sivas (TR); Caglayan Gayretli, Sivas (TR); Kazim Gayretti, Sivas (TR); Ozmen Akay, Sivas (TR); Sefika Akbas, Sivas (TR); Seda Aliskan, Sivas (TR)

(73) Assignee: Bipore Medical Devices, Inc., Northvale, NJ (US)

( * ) Notice: Subject to any disclaimer, the term of this patent is extended or adjusted under 35 U.S.C. 154(b) by 284 days.

(21) Appl. No.: 12/070,901

(22) Filed: Feb. 19, 2008

(65) Prior Publication Data

US 2009/0209914 A1 Aug. 20, 2009

(51) Int. Cl.
*A61M 5/178* (2006.01)
*A61M 39/06* (2006.01)

(52) U.S. Cl.
CPC .... *A61M 39/0613* (2013.01); *A61M 2039/066* (2013.01); *A61M 2039/0633* (2013.01)

(58) Field of Classification Search
CPC ............... A61M 39/0613; A61M 2039/0633; A61M 2039/066
USPC ........... 251/149.1; 604/167.01–167.06, 256, 604/167.02
See application file for complete search history.

(56) References Cited

U.S. PATENT DOCUMENTS

| | | | |
|---|---|---|---|
| 4,436,519 A | 3/1984 | O'Neill | |
| 4,857,062 A * | 8/1989 | Russell | 604/256 |
| 4,895,346 A * | 1/1990 | Steigerwald | 251/149.1 |
| 4,978,341 A * | 12/1990 | Niederhauser | 604/256 |
| 5,106,054 A | 4/1992 | Mollenauer et al. | |
| 5,114,408 A | 5/1992 | Fleischhaker et al. | |
| 5,269,771 A * | 12/1993 | Thomas et al. | 604/539 |
| 5,350,364 A * | 9/1994 | Stephens et al. | 604/167.06 |
| 5,397,335 A * | 3/1995 | Gresl et al. | 606/185 |
| 5,409,463 A * | 4/1995 | Thomas et al. | 604/167.04 |
| 5,492,304 A * | 2/1996 | Smith et al. | 251/149.1 |
| 5,601,540 A * | 2/1997 | Stevens | 604/533 |
| 6,099,505 A * | 8/2000 | Ryan et al. | 604/167.04 |
| 6,632,200 B2 * | 10/2003 | Guo et al. | 604/247 |
| 7,063,685 B2 | 6/2006 | Rome | |
| 7,081,106 B1 | 7/2006 | Guo et al. | |
| 7,226,433 B2 | 6/2007 | Bonnette et al. | |
| 7,578,803 B2 * | 8/2009 | Rome et al. | 604/167.04 |
| 2004/0127853 A1 * | 7/2004 | Howell | 604/167.01 |

* cited by examiner

*Primary Examiner* — Theodore Stigell
(74) *Attorney, Agent, or Firm* — Klauber & Jackson LLC

(57) ABSTRACT

A sealing arrangement for a medical introducer having a distal end for introduction into a patient's blood vessel. The introducer includes a flexible sealing member having an aperture for introduction of a guide wire or other medical device therethrough. A constraining structure, such as a washer, tightly contacts and surrounds the sealing member just proximal to an enlarged diameter flange at the distal end of the sealing member. The inner diameter of the constraining member is less than the outer diameter of the flange providing a constraint on the sealing member and lessening the distortion of the sealing member normally occasioned when a device is pulled outwardly or proximally through the introducer away from the patient. When the constraining structure is a washer, the washer is easily assembled to the introducer by simply being fitted into an annular notch formed just proximal to the distal end of the sealing member.

16 Claims, 2 Drawing Sheets

SEALING ARRANGEMENT FOR MEDICAL INTRODUCER

FIELD OF THE INVENTION

The present invention relates to a medical introducer for providing communication with the arterial system of a patient and, more particularly, to a medical introducer having a seal for sealing against a device inserted through the introducer such as a guide wire, a dilator or the like.

BACKGROUND OF THE INVENTION

An introducer is used in the medical field to establish and provide access to the arterial system of a patient. Once established, the introducer provides a means of access to the arterial system for certain instruments or devices, and specifically, that device can be a guide wire that passes through the introducer wherein the distal end of the guide wire is located in the particular desired artery of the patient.

In a typical introduction of a guide wire into a patient, a needle is first inserted into the patient with its distal end positioned in the artery. A guide wire is then normally slid through the needle such that the distal end of the guide wire is located within that particular artery. At that point, the needle is removed while the guide wire remains in its position in the artery. An introducer, with a dilator, is then inserted over the guide wire into the artery. The dilator is then removed while the introducer is retained in that position with the guide wire passing therethrough such that other medical devices can be threaded over and along the guide wire through the introducer into the particular artery.

For example, a stent can be introduced through the introducer and located at the desired location with a balloon that is inflated to emplace the stent and the balloon removed.

In any case, there must be a seal between the introducer and the particular device that passes through the introducer to be used in treating the patient. One of the chronic problems, however with such devices is that the sealing function of the introducer against the particular device is normally carried out by the use of a flexible or elastomeric material and, over time, that material becomes fatigued or distorted and eventually result in leaking through the introducer.

Further, the problem occurs when there is no device at all passing through the introducer, that is, when a device is removed by pulling it outwardly from the introducer, there is a tendency to distort the seal as that device is pulled through the seal and thus create a leakage situation. Basically, the pulling of a device outwardly away from the patient through the seal during the removal of that device causes the seal to pull outwardly and create a distortion of that seal.

It would, therefore, be desirable to have an arrangement that provides a good, improved seal within the introducer that would provide a seal between the introducer and any device that passes through the introducer and also lessen the problem of leaking seals.

It would be further advantageous to have a seal that does not experience the normal distortion that occurs when a device is pulled outwardly from the introducer so that the leaking resulting from that distortion is lessened.

It would be further advantageous to have a seal arrangement that is relatively inexpensive to implement and which fits readily within the normal housing of an introducer such that the assembly of an introducer is not made unduly difficult.

BRIEF SUMMARY OF THE INVENTION

Accordingly, the present invention relates to a sealing arrangement that enhances the ability of an introducer to maintain a seal over long periods of time against a device passing through the introducer or with no device present and thus reduce the problem of leaking resulting from material fatigue and/or distortion.

With the present invention, there is a medical introducer that provides communication with an artery within the arterial system of a patient. The introducer comprises an introducer housing that has a proximal end and a distal end connected to a tube that is introduced into the artery of the patient. Within the introducer housing, there is a sealing member comprised of a flexible material such as silicone rubber and which has a proximal end, a distal end and a closable aperture extending therethrough. The aperture is the sole path through the introducer housing for a guide wire or like device and, since the introducer body is in fluid communication with the patient's artery, the sealing member forms a seal that surrounds and seals against any such device passing through the introducer housing as well as against the passage of fluid when no device is present.

With the present invention, the sealing member is reinforced by a constraining structure, such as a washer, that tightly surrounds and contacts the outer annular surface of the sealing member to alleviate the creation of distortion of the sealing member that is normally experienced when a device is removed from an introducer by pulling the device outwardly or proximally through the introducer i.e. away from the patient. The distal end of the sealing member i.e. toward the patient has a flange having an outer diameter that is larger than the inner diameter of the constraining structure such that, as a device is pulled outwardly, the distal end of the sealing member remains in tact and does not experience the distortion otherwise created by the outward movement of the particular device.

These and other features and advantages of the present invention will become more readily apparent during the following detailed description taken in conjunction with the drawings herein.

DETAILED DESCRIPTION OF THE INVENTION

Figure 1:
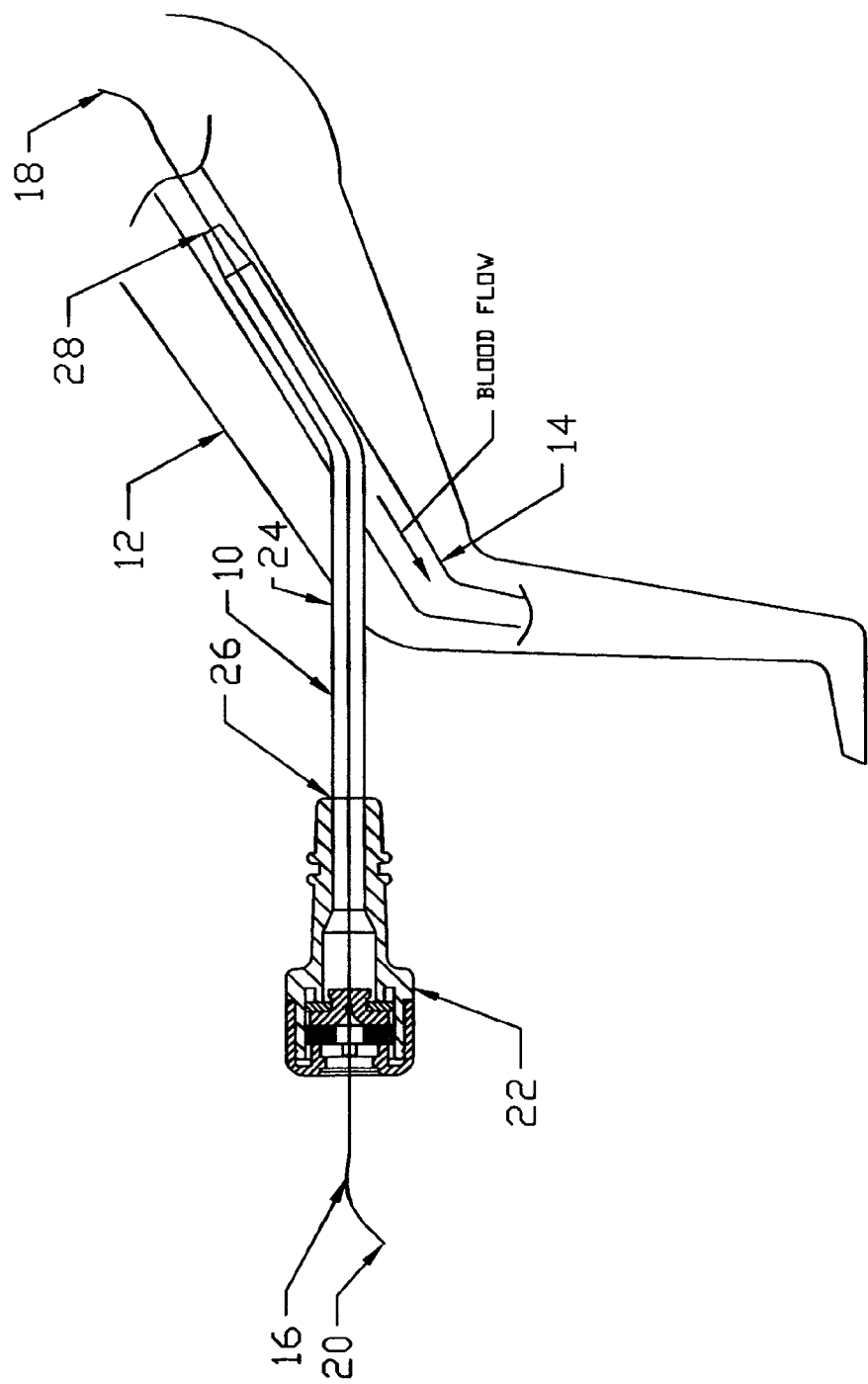
FIG. 1 is a schematic view of an introducer being utilized with a patient.

Referring now to FIG. 1, there is shown a schematic view of an introducer 10 constructed in accordance with the present invention and in position being used with a patient.

As can be seen, FIG. 1 is illustrating the leg 12 of a patient with an artery 14 therein for the purpose of explaining the present invention. The direction of the blood flow in the artery 14 is illustrated by the arrow A. Other areas of the patient's arterial system can, of course, by accessed with the use of the present invention.

Accordingly, there can be seen a guide wire 16 that can be located and emplaced by conventional techniques such that its distal end 18 is located in the artery 14 which is the artery desired by the physician to be accessed and a proximal end 20 extending external of the introducer 10. The introducer 10 includes an introducer housing 22 through which the guide wire 16 passes and a tube 24 having a central lumen having a proximal end 26 affixed to and in fluid communication with the introducer housing 22 and a distal end 28 positioned within the artery 14 of the patient.

As can therefore be seen, with the introducer housing 22 directly in fluid communication with the artery 14 of the patient, it is important that there be a seal within the introducer housing 22 to prevent fluid from passing proximally through the introducer housing 22, including a path created by the guide wire 16 that extends fully through the introducer housing 22.

Figure 2:
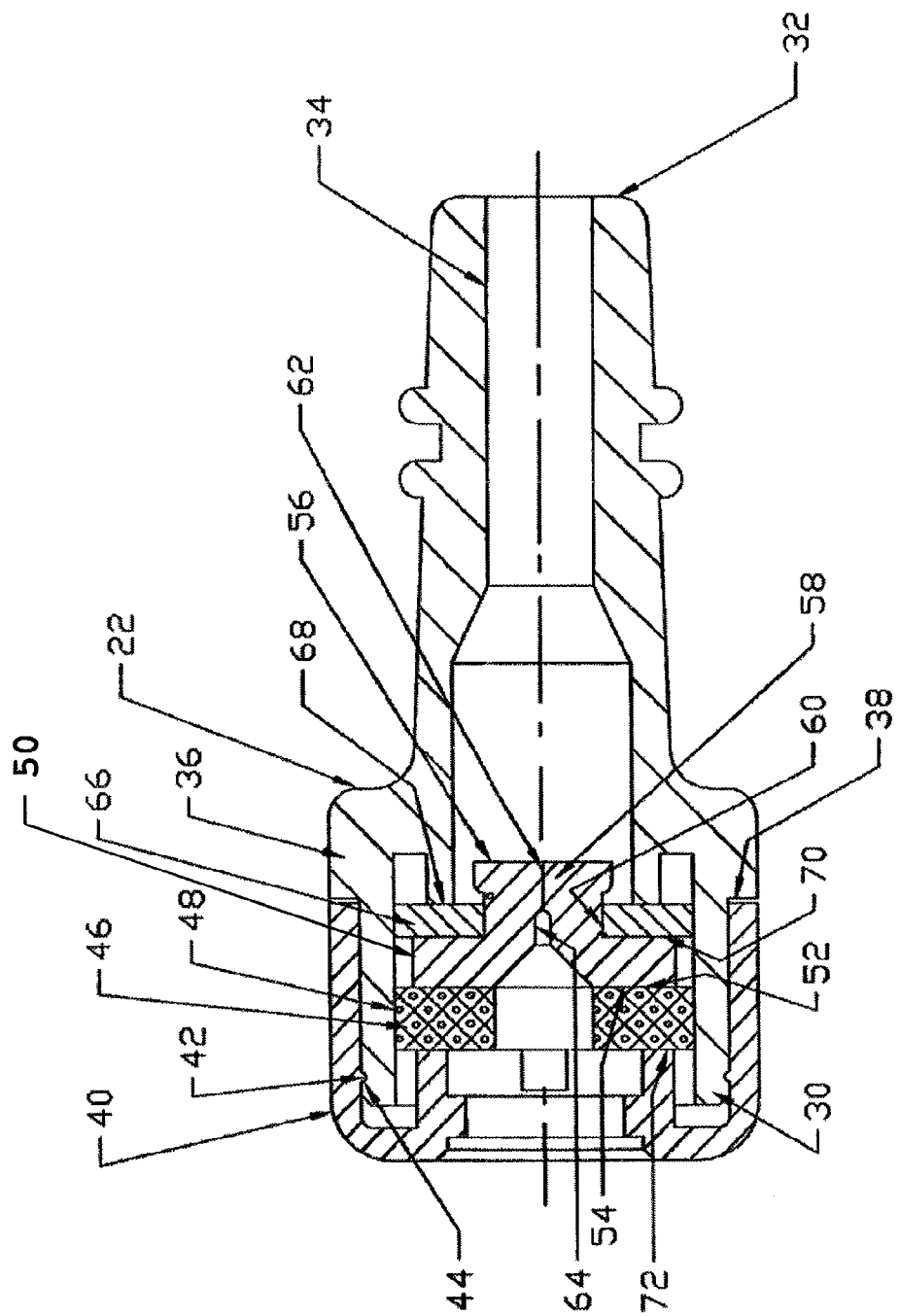
FIG. 2 is a lateral cross sectional view of the introducer of the present invention.

Turning next to FIG. 2, there is a lateral cross sectional view of the introducer housing 22 and illustrating the sealing arrangement of the present invention. The introducer housing 22 has a proximal end 30 and a distal end 32. The distal end 32 has a reduced diameter area 34 in order to accept the tube 24 (FIG. 1) to be affixed thereto and the introducer housing 22 increases to a larger diameter area 36 with an indented circular face 38 facing proximally. The proximal end 30 of the introducer housing 22 then continues proximally at that reduced diameter. A hub 40 covers the proximal end 30 of the introducer housing 22 and the hub 40 may be affixed to the proximal end 30 by a snapping action with a small annular protrusion 42 formed in the hub 40 snapping into a similar dimensioned annular groove 44 formed in the proximal end 30 of the introducer housing 22.

Within the introducer housing 22 is a circular foam disc 46 that fits snugly within the internal surface 48 of the introducer housing 22 and which may be constructed of polyurethane. Further, there is a sealing member 50 that is located within the introducer housing 22 and having a proximal end 52 forming a circular outer flange 54 having a diameter that is less than the inner diameter of the internal surface 48 of introducer housing 22 and a cylindrical distal end 56. As can be seen, the distal end 56 has an enlarged diameter circular flange 58 that forms an annular notch 60 having a lesser outer diameter than the circular flange 58 and the annular notch 60 is located just proximal to the circular flange 58. The sealing member 50 can be constructed of a flexible material such as silicone rubber.

An aperture 62 is provided that passes entirely through the sealing member 50 and that aperture is enlarged at the distal end 64 thereof to facilitate the passing of a device through the sealing member 50. As can be seen, any device that is passed through the introducer housing 22 passes through the aperture 62 and thus it is important, as stated, that there be a seal between the aperture 62 of the sealing member 50 and any such device as well as a sealing of the aperture 62 itself when no device at all is present.

As such, the sealing function of the sealing member 50 is enhanced by the presence of a constraining structure, such as provided by a washer 66 that surrounds the sealing member 50 and contacts and constrains that sealing member 50 along the outer surface of the annular notch 60. The washer 66 can be comprised of any material that can provide a constraint to the sealing member 50 and can be a rigid or flexible material; however, preferably the washer 66 is an elastic material having a memory. The washer 66 tightly surrounds and contacts the external surface of the annular notch 60 of the sealing member 50 to retain the washer 66 in its desired position.

The presence of the constraining structure, i.e. washer 66 enhances the sealing ability of the sealing member 50 and retains the aperture tightly against any device that is passed through the aperture 62 as well as where no such device is present.

Thus, when a device is removed from the patient by pulling it outwardly in the proximal direction through the introducer 10 and thus, through the sealing member 50, the presence of the washer 66 maintains the integrity of the sealing member 50 and prevents the sealing member 50 from being distorted as the device is removed. As can be seen, the circular flange 58 has an outer diameter that is larger that the inner diameter of the washer 66 and therefore the distal end 56 of the sealing member 50 is prevented from being distorted by the withdrawal of a device from the sealing member 50 that is normally experienced when a device is pulled proximally outwardly, that is, away from the patient, through that sealing member 50.

As such, even when the device has been fully removed, the lack of the normal distortion experienced with that removal maintains the sealing ability of the sealing member 50. In the exemplary embodiment, the constraining structure is the washer 66, however, other structures could be used, including the housing itself that encircles and contacts the outer surface of the sealing member just proximal to the enlarged diameter circular flange 58.

In addition, as can now be seen, the addition and assembly of the washer 66 to the overall assembly making up the introducer 10 is readily facilitated, that is, the washer 66 can be forced over the circular flange 58 of the distal end 56 of the sealing member 50 to be retained in the annular notch 60. Thereafter the introducer 10 can be assembled readily by simply inserting the sealing member 50 combined with the washer 66 into the interior of the introducer housing 22 such that the distal surface 68 of the washer 66 is pressed against and thereby sealed to the introducer housing 22 while the proximal surface 70 of the washer 66 pressed again and sealed to the sealing member 50.

Thereafter, the foam disc 46 can be installed by inserting into the introducer housing 22 and the foam disc 46 presses against the proximal end 52 of the sealing member 50. The hub 40 is then snap fitted to the proximal end 30 of the introducer housing 22 sealing the aforementioned components together by the hub flange 72 pressing against the foam disc 46.

Thus, the washer 66 is easily installed during the assembly of an introducer and yet provides additional sealing effectiveness to the sealing of the introducer 10 against any device that may pass through the aperture 62 by preventing distortion of the sealing member 50 when a device is withdrawn proximally through the introducer 10.

Those skilled in the art will readily recognize numerous adaptations and modifications which can be made to the introducer of the present invention which will result in an improved device and method of using the same, yet all of which will fall within the scope and spirit of the present invention as defined in the following claims. Accordingly, the invention is to be limited only by the following claims and their equivalents.

What is claimed is:

1. A medical introducer for providing communication with the arterial system of a patient, the introducer comprising:

an introducer housing having a proximal end, a distal end and an inner surface, a flexible sealing member having an inner surface and an outer surface, the sealing member located within the housing having a closable aperture formed therein to allow an instrument to pass through the introducer housing and to seal the aperture when no instrument is passing therethrough, the inner surface of the sealing member forming a seal against an instrument and having a distal end forming an enlarged diameter circular flange and a proximal end having an enlarged diameter, wherein an annular notch is formed in the sealing member just proximal to and positioned between the enlarged diameter circular flange and the enlarged diameter proximal end, the annular notch having an outer surface having a lesser diameter than the enlarged diameter circular flange and the enlarged diameter proximal end, and a constraining structure surrounding and contacting the outer surface of the annular notch, the constraining structure having an internal diameter less than the enlarged diameter circular flange and the enlarged diameter proximal end, the constraining structure in contact with and held in place by the inner surface of the housing, wherein the constraining structure prevents distortion of the annular notch of the sealing member while allowing the enlarged diameter circular flange to expand outwardly as an instrument is passed through the sealing member.

2. The medical introducer of claim 1 wherein the constraining structure is a washer.

3. The medical introducer of claim 2 wherein the washer has a surface facing toward the proximal end of the introducer housing that seats against the proximal end of the sealing member.

4. The medical introducer of claim 2 wherein the washer is retained within the introducer housing by being sandwiched between the introducer housing and the proximal end of the sealing member.

5. The medical introducer of claim 2 wherein a hub is affixed to the proximal end of the introducer housing and holds the washer against the housing.

6. The medical introducer of claim 2 wherein the washer is comprised of a material having a memory.

7. The medical introducer of claim 2 wherein the washer is comprised of polyurethane.

8. A method of assembling a medical introducer comprising the steps of:

providing an introducer housing having a distal end, a proximal end and an inner surface and having an internal passageway along a longitudinal axis of the introducer housing;

providing a sealing member adapted to fit into the passageway, the sealing member having a closable aperture to seal the aperture, an elongated distal end having a circular flange, and a proximal end having an enlarged diameter and an annular notch having an outer surface located just proximal to the elongated distal end and distal to the enlarged diameter of the proximal end;

attaching a constraining structure to the sealing member encircling and contacting the outer surface of the annular notch of the sealing member and contacted by and held in place by the inner surface of the introducer housing and wherein the constraining structure encircles and seals about the annular notch while allowing the circular flange of the distal end to expand outwardly; and attaching a hub to the proximal end of the introducer housing to secure the sealing member in a sealed relationship to the introducer housing.

9. The method of claim 8 wherein the constraining structure is a washer.

10. The method of claim 9 wherein the step of attaching a constraining structure encircling and contacting the outer surface of the distal end of the sealing member comprises attaching the washer to encircle the sealing member and inserting the sealing member and washer into the introducer housing prior to the step of attaching a hub to the proximal end of the introducer housing to secure the sealing member in a sealed relationship to the introducer housing.

11. The method of claim 10 wherein the step of inserting the sealing member and washer into the introducer housing includes the step of sealing the washer against the introducer housing.

12. The method of claim 9 wherein the step of attaching a washer comprises attaching a washer comprised of a material having a memory.

13. A medical introducer for providing communication with the arterial system of a patient, the introducer comprising:

an introducer housing having a proximal end, a distal end, and an inner surface, a flexible sealing member having an inner surface and an outer surface, the sealing member located within the housing having a closable aperture formed therein to allow an instrument to pass through the introducer housing and to seal the aperture when no instrument is passing therethrough, the inner surface of the flexible sealing member adapted to seal against an instrument and having a proximal end having an enlarged diameter, an elongated distal end having an enlarged diameter circular flange, and an annular notch located just proximal to and located between the elongated distal end and the enlarged diameter proximal end, the annular notch having an outer surface, a foam disc located within the introducer housing proximally located with respect to the flexible sealing member, a constraining structure surrounding the sealing member to contact the outer surface annular notch, the constraining structure in contact with and held in place by the inner surface of the housing, wherein the constraining structure encircles and seals about the annular notch to prevent distortion of the notch and to allow the enlarged diameter circular flange to flex outwardly as an instrument is passed through the sealing member, and a hub affixed to the proximal end of the introducer housing, the hub contacting the foam disc to retain the foam disc and the flexible sealing member in position within the introducer housing.

14. The medical introducer of claim 13 wherein the constraining structure is a washer.

15. The medical introducer of claim 13 wherein the hub is snap fitted to the introducer housing.

16. The medical introducer of claim 13 wherein the constraining structure is comprised of a material having a memory.

* * * * *